United States Patent [19]
Tenten et al.

[11] Patent Number: 5,637,546
[45] Date of Patent: Jun. 10, 1997

[54] PREPARATION OF CATALYTICALLY ACTIVE POLY-METAL OXIDE MATERIALS WHICH CONTAIN THE ELEMENTS V AND MO IN OXIDE FORM AS BASIC COMPONENTS

[75] Inventors: Andreas Tenten, Neustadt; Ulrich Hammon; Peter Weidlich, both of Mannheim, all of Germany

[73] Assignee: BASF Aktiengesellschaft, Ludwigshafen, Germany

[21] Appl. No.: 628,640

[22] PCT Filed: Oct. 11, 1994

[86] PCT No.: PCT/EP94/03345

§ 371 Date: Apr. 19, 1996

§ 102(e) Date: Apr. 19, 1996

[87] PCT Pub. No.: WO95/11081

PCT Pub. Date: Apr. 27, 1995

[30] Foreign Application Priority Data

Oct. 21, 1993 [DE] Germany .................. 43 35 973.6

[51] Int. Cl.⁶ ...................................... B01J 23/22
[52] U.S. Cl. ...................................... 502/312; 502/311
[58] Field of Search ........................... 502/311, 312, 502/38, 54, 55

[56] References Cited

U.S. PATENT DOCUMENTS

| 4,062,885 | 12/1977 | Mekhtiev et al. | 260/465 |
| 4,075,283 | 2/1978 | Shiraishi et al. | 423/239 |
| 4,356,114 | 10/1982 | Kadowaki et al. | |

FOREIGN PATENT DOCUMENTS 31 19 586  2/1982  Germany.

OTHER PUBLICATIONS

Catal. Rev.–Sci. Eng., vol. 35, No. 2, pp. 213–259, 1993, T.V. Andrushkevich, "Heterogeneous Catalytic Oxidation of Acrolein to Acrylic Acid: Mechanism and Catalysts".

Chem., vol. 616, No. 43, pp. 95–106, 1991, J. Tichy, et al., "Active Component of Mo–V–O Catalysts in the Process of Acrolein Oxidation".

*Primary Examiner*—Glenn A. Caldarola
*Assistant Examiner*—Alexander G. Ghyka
*Attorney, Agent, or Firm*—Oblon, Spivak, McClelland, Maier & Neustadt, P.C.

[57] ABSTRACT

In a process for the preparation of catalytically active poly-metal oxide materials containing Mo and V, a catalyst intermediate is calcined at from 300° to 450° C. in a gas atmosphere which, in addition to inert gases and/or steam, consists of from 0.5 to 4% by volume of $O_2$ and, averaged over the calcination time, from 1 to 8% by volume of $NH_3$.

2 Claims, No Drawings

PREPARATION OF CATALYTICALLY ACTIVE POLY-METAL OXIDE MATERIALS WHICH CONTAIN THE ELEMENTS V AND MO IN OXIDE FORM AS BASIC COMPONENTS

The present invention relates to a process for the preparation of catalytically active poly-metal oxide materials which contain the elements V and Mo in oxide form as basic components, in which an intimate dry mixture is prepared from starting compounds which contain the elemental constituents of the poly-metal oxide materials and said mixture is calcined at from 300° to 450° C. in a gas atmosphere consisting of oxygen, ammonia and, as a residual amount, steam and/or inert gas.

Zesz. Nauk.-Politech. Lodz., Chem. 616 (43) (1991), 95–106, discloses that poly-metal oxide materials which contain the elements V and Mo in oxide form as basic components are suitable as catalysts for the catalytic gas-phase oxidation of acrolein to acrylic acid. Furthermore, the abovementioned publication discloses that such catalytically active poly-metal oxide materials can be produced by a method in which catalyst intermediates are calcined first in the presence of air and then in the presence of a gas mixture consisting of acrolein, oxygen and inert gases. Catal. Rev.-Sci. Eng. 35 (2) (1993), 213–259, recommends a corresponding preparation process. However, the disadvantage of this procedure is that acrolein-containing calcination atmospheres cannot be handled in conventional calcination ovens.

DE-31 19 586 C2 discloses that a catalytically active poly-metal oxide material which contains the elements V and Mo in oxide form as basic components can be produced by preparing an intimate dry mixture containing ammonium ions from starting compounds which contain the elemental constituents of the poly-metal oxide materials and calcining said mixture at 380° C. in a gas stream which contains 1% by volume of oxygen in addition to steam and inert gases. The resulting poly-metal oxide material is recommended in DE-31 19 586 C2 as a catalyst for the catalytic gas-phase oxidation of acrolein to acrylic acid.

Owing to the content of ammonium ions in the material to be calcined, the calcination atmosphere according to DE-31 19 586 C2 does of course contain ammonia. DE-31 19 586 C2 does not envisage any effect of the ammonia content of the calcination atmosphere on the catalyst activity and selectivity.

The present invention is based on the surprising discovery that, in the case of poly-metal oxide materials containing V and Mo as basic components in oxide form, a defined $NH_3$ content of the calcination atmosphere in combination with a defined $O_2$ content thereof leads to catalytically active materials which have higher catalyst activity and selectivity when used as catalysts for obtaining acrylic acid from acrolein by catalytic gas-phase oxidation.

Accordingly, we have found a process for the preparation of catalytically active poly-metal oxide materials which contain the elements V and Mo in oxide form as basic components, in which an intimate dry mixture is prepared from starting compounds which contain the elemental constituents of the poly-metal oxide materials and said mixture is calcined at from 300° to 450° C., with the proviso that the gas atmosphere in which the calcination is carried out is composed of from 0.5 to 4, preferably from 1 to 2, % by volume of $O_2$ throughout the calcination, from 1 to 8% by volume, averaged over the total duration of the calcination, of $NH_3$ and steam and/or inert gas as the remaining amount.

The $NH_3$ content of the calcination atmosphere, averaged over the total duration of the calcination, is from 1 to 6, particularly preferably from 4 to 6, % by volume.

The calcination is particularly preferably carried out at a calcination temperature of from 300° to 350° C. (calcination stage I) for from 50 to 95% of the total calcination time (as a rule from 3 to 15 hours) and at a calcination temperature of from 380° to 450° C. for from 5 to 50% of the total calcination time in a subsequent calcination stage II.

It is advantageous if the $NH_3$ content of the calcination atmosphere, averaged over the total duration of calcination stage I, is from 5 to 8% by volume and the $NH_3$ content of the calcination atmosphere, averaged over the total duration of calcination stage II, is $\leq 4$, preferably from 1 to 3, % by volume.

Particularly advantageously, the abovementioned numerical $NH_3$ contents are fulfilled not only as time averages but are present as such at all times in the calcination atmospheres of calcination stages I and II.

The novel process proves advantageous in particular for catalytically active poly-metal oxide materials having a molar Mo:V ratio of from 12:1 to 12:6.

The novel products of the process advantageously also contain W and/or Nb, in a molar ratio to Mo of from 0.2:12 to 4:12. It is also advantageous if the catalytically active poly-metal oxide materials contain Cu over and above the abovementioned metallic elements and do so in a molar ratio to Mo of from 0.5:12 to 18:12.

Particularly advantageous novel products of the process have the following general stoichiometry I

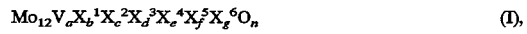

$$Mo_{12}V_a X_b^1 X_c^2 X_d^3 X_e^4 X_f^5 X_g^6 O_n \qquad (I),$$

where $X^1$ is W, Nb, Ta, Cr and/or Ce, $X^2$ is Cu, Ni, Co, Fe, Mn and/or Zn, $X^3$ is Sb and/or Bi, $X^4$ is at least one or more alkali metals, $X^5$ is at least one or more alkaline earth metals, $X^6$ is Si, Al, Ti and/or Zr, a is from 1 to 6, b is from 0.2 to 4, c is from 0.5 to 18, d is from 0 to 40, e is from 0 to 2, f is from 0 to 4, g is from 0 to 40 and n is a number which is determined by the valency and frequency of the elements in I other than oxygen.

Among these products, those in which $X^1$ is W, Nb and/or Cr, $X^2$ is Cu, Ni, Co and/or Fe, $X^3$ is Sb, $X^4$ is Na and/or K, $X^5$ is Ca, Sr and/or Ba, $X^6$ is Si, Al and/or Ti, a is from 2.5 to 5, b is from 0.5 to 2, c is from 0.5 to 3, d is from 0 to 2, e is from 0 to 0.2, f is from 0 to 1, g is from 0 to 15 and n is a number which is determined by the valency and frequency of the elements in I other than oxygen are preferred.

However, the following poly-metal oxide materials II $$Mo_{12}V_aX_b^1X_c^2X_f^5X_g^6O_n \quad \text{(II)},$$

where
X$^1$ is W and/or Nb,
X$^2$ is Cu and/or Ni,
X$^5$ is Ca and/or Sr,
X$^6$ is Si and/or Al,
a is from 3 to 4.5,
b is from 1 to 1.5,
c is from 0.75 to 2.5,
f is from 0 to 0.5,
g is from 0 to 8 and
n is a number which is determined by the valency and frequency of the elements in I other than oxygen,
are very particularly preferred, being direct products of the process.

The novel process starts from conventional suitable sources of the poly-metal oxide materials and produces from them a very intimate, preferably finely divided dry mixture which is then subjected to calcination, which may be effected before or after shaping to give catalyst elements having a specific geometry. As is generally known, all that is important is that the sources are either already oxides or are compounds which can be converted into oxides by heating, at least in the presence of oxygen. In addition to the oxides, particularly suitable starting compounds are therefore halides, nitrates, formates, oxalates, acetates, carbonates or hydroxides. Useful starting compounds of Mo, V, W and Nb are also their oxo compounds (molybdates, vanadates, tung-states and niobates) and the acids derived from these.

The starting compounds may be mixed in dry or wet form to obtain an intimate mixture. If mixing is carried out in dry form, the starting compounds are advantageously used in the form of finely divided powders and are compressed (for example tableted) after the mixing process, for example to give catalyst elements having the desired geometry, which are then subjected to the calcination.

However, said starting compounds are preferably mixed in wet form to obtain the intimate mixture. The starting compounds are usually mixed with one another in the form of an aqueous solution or suspension. Thereafter, the aqueous material is dried and then calcined. The drying process is preferably carried out immediately after the preparation of the aqueous mixture and is effected by spray drying (the outlet temperatures are as a rule from 100° to 150° C.). The powder obtained can be molded directly by compression. However, it frequently proves to be too finely divided for direct further processing and is therefore then advantageously kneaded with the addition of water.

The pasty material obtained is then either molded to give the desired catalyst geometry, dried and then subjected to the calcination (leads to unsupported catalysts) or calcined without molding and then milled to give a finely divided (<80 μm) powder, which is applied, usually with the addition of a small amount of water and, if required, further conventional binders, as a moist material to inert carriers. After the end of the coating process, drying is carried out again and the ready-to-use coated catalyst is thus obtained. In principle, however, the calcined powder may also be used as a powder catalyst. If the starting compounds are mixed in the form of an aqueous solution, it is also possible for inert porous carriers to be impregnated with said solution and dried and then calcined to give supported catalysts.

In the preparation of coated catalysts, coating of the carriers may also be carried out prior to the calcination, for example with the moistened spray powder. Carriers suitable for coated catalysts are, for example, porous or nonporous aluminas, silica, thorium dioxide, zirconiumdioxide, silicon carbide or silicates, such as magnesium silicate or aluminum silicate. The carriers may have a regular or irregular shape, carriers having a regular shape and pronounced surface roughness, for example spheres or hollow cylinders, being preferred. Among these in turn, spheres are advantageous.

The use of essentially non-porous spherical steatite carriers which have a rough surface and whose diameter is from 1 to 6 mm, preferably from 4 to 5 mm, is very particularly advantageous. The layer thickness of the active material is advantageously chosen in the range from 50 to 500 μm, preferably from 100 to 250 μm.

The calcination atmosphere required according to the invention can be realized in a simple manner, for example, by carrying out calcination in an oven through which a gas mixture which has a corresponding composition with regard to O$_2$, NH$_3$ and inert gases/steam is passed. In a less preferable embodiment, the required average ammonia content of the calcination atmosphere may also be achieved by incorporating a corresponding amount of ammonium ions into the dry material to be calcined, said ions decomposing in the course of the calcination with evolution of NH$_3$. Addition of NH$_3$ over and above this is not absolutely essential according to the invention. The ammonium ions can advantageously be introduced into the dry mixture by using the ammonium salts of the oxo acids of the corresponding metals as sources of the elements Mo, V, W or Nb. Examples of these are ammonium metaniobate, ammonium metavanadate, ammonium heptamolybdate tetrahydrate and ammonium paratungstate heptahydrate. However, independently of the starting compounds required as sources of the catalyst constituents, it is of course also possible for ammonium donors, such as NH$_4$NO$_3$ or ammonium acetate, which decompose completely into gaseous compounds on calcination, to be incorporated into the dry mixture to be calcined.

According to the invention, however, the incorporation of ammonium ions alone into the dry mixture to be calcined is not sufficient. Instead, the required average ammonia content of the calcination atmosphere is obtained only when the amount of catalyst to be calcined is furthermore adapted in a corresponding manner to the internal volume of the calcination oven. This NH$_3$ evolution from the catalyst intermediate and the external supply of NH$_3$ can of course also be used in combination. A through-circulation oven fed with the corresponding gas mixtures is advantageously used as the calcination oven. Where there is only NH$_3$ evolution from the catalyst intermediate (of the dry mixture to be calcined), the NH$_3$ content of the calcination atmosphere usually passes through a maximum as a function of the calcination time (as a rule a few hours; the required calcination time decreases with the calcination temperature). Satisfactory catalyst activities are obtained in particular when the NH$_3$ content of the calcination atmosphere as a function of the calcination time is as follows:

| Calcination time (expressed in % of total time) | % by volume of NH$_3$ |
|---|---|
| 0–10 | 0–5 |
| >10–15 | 3–10 |
| >15–25 | 8–16 |
| >25–40 | 6–14 |
| >40–60 | 1.5–8 |
| >60–100 | 0–2 |

Particularly well defined calcination conditions can be realized using a belt-type calcination oven. The term inert gases is understood as meaning all those gases which undergo no chemical reaction with the material to be calcined during the calcination. Examples of inert gases are $N_2$ and noble gases. Steam is present in the calcination atmosphere in particular when the catalyst intermediate contains water of hydration.

As a rule, the steam content of the calcination atmosphere never exceeds 20% by volume at any time during the calcination.

The poly-metal oxide materials obtained in the novel process are particularly suitable as catalysts for the catalytic gas-phase oxidation of acrolein to acrylic acid. With regard to this reaction, they have higher activity and effect acrylic acid formation with higher selectivity. This is due to the fact that the specific calcination conditions, particularly with regard to the elements V and Mo, lead to a particularly advantageous distribution of various oxidation states in the poly-metal oxide materials resulting according to the invention. The catalytic gas-phase oxidation of acrolein to acrylic acid is carried out in a manner known per se. The oxygen required in a gas-phase oxidation may be added, for example, in the form of air as well as in pure form. Owing to the high heat of reaction, the reactants are preferably diluted with inert gas, such as $N_2$, $CO_2$, lower hydrocarbons, recycled reaction exit gases and/or steam. In the acrolein oxidation, an acrolein:oxygen:steam:inert gas volume ratio of 1:(1–3):(0–20):(3–30), preferably 1:(1–3):(0.5–10):(7–18), is usually established. Acrolein which was produced by the catalytic gas-phase oxidation of propene is usually used in the process. As a rule, the acrolein-containing reaction gases of this propene oxidation are used without intermediate purification. The reaction pressure is as a rule from 1 to 3 bar and the total space velocity is preferably from 1000 to 3500 1(S.T.P.) per 1 per h.

Typical multi-tube fixed-bed reactors are described, for example, in DE-A 28 30 765, DE-A 22 01 525 or U.S. Pat. No. 3 147 084.

In addition to the catalytic gas-phase oxidation of acrolein to acrylic acid, the novel products for the process are, however, also capable of catalyzing the gas-phase oxidation of other organic compounds, in particular other alkanes, alkanols, alkanals, alkenes and alkenols of preferably 3 to 6 carbon atoms (e.g. propylene, methacrolein, tert-butanol, methyl ether or tertbutanol, isobutene, isobutane or isobutyraldehyde) to olefinically unsaturated aldehydes and/or carboxylic acids as well as the corresponding nitriles (ammoxidation, especially of propene to acrylonitrile and of isobutene or tert-butanol to methacrylonitrile). The preparation of acrolein, methacrolein and methacrylic acid may be mentioned by way of example. However, they are also suitable for the oxidative dehydrogenation of olefinic compounds.

Unless stated otherwise, the conversion, selectivity and residence time are defined as follows in this publication:

Conversion $C$ of acrolein (%) =

$$\frac{\text{Number of mol of converted acrolein}}{\text{Number of mol of acrolein used}} \times 100;$$

Selectivity of acrylic acid formation (%) =

$$\frac{\text{Number of mol of acrolein converted to acrylic acid}}{\text{Total number of mol of acrolein reacted}} \times 100;$$

Residence time (sec) =

$$\frac{\text{Reactor volume filled with catalyst (1)}}{\text{Throughput of synthesis gas (1(S.T.P.)/h)}} \times 3600.$$

An active material leading to the same conversion under otherwise unchanged reaction conditions at a lower temperature has a higher activity.

EXAMPLES a) Preparation of a catalyst intermediate 190 g of copper(II) acetate monohydrate were dissolved in 2700 g of water to give a solution I. 860 g of ammonium heptamolybdate tetrahydrate, 143 g of ammonium metavanadate and 126 g of ammonium paratungstate heptahydrate were dissolved in succession in 5500 g of water at 95° C. to give a solution II. Solution I was stirred all at once into solution II, and the aqueous mixture was spray-dried at an outlet temperature of 110° C. The spray powder was then kneaded with 0.15 kg of water per kg of powder.

b) Calcination

The catalyst intermediate obtained in a) was calcined in a through-circulation oven fed with an oxygen/nitrogen mixture. In all cases, the oxygen content was adjusted so that the $O_2$ content at the outlet of the through-circulation oven was 1.5% by volume. In the calcination, the paste from a) was first heated to 300° C. at a rate of 10K/min and kept at this temperature for 6 hours. Thereafter, heating was carried out at a rate of 10K/min to 400° C. and this temperature was maintained for a further hour. In order to obtain various ammonia contents of the calcination atmosphere, on the one hand the oven loading O (g of catalyst intermediate per 1 of internal volume of the through-circulation oven), the inlet volume flow rate IF (1(S.T.P.)/h) of the oxygen/nitrogen mixture and the residence time R (sec) of the oxygen/nitrogen feed (ratio of internal volume of the through-circulation oven to the volume flow rate of the oxygen/nitrogen mixture fed in) were varied. Furthermore, the oxygen/nitrogen gas mixture fed in contained a certain volume V of $NH_3$ (% by volume) in some cases. The through-circulation ovens used had internal volumes of 3 1 and 40 1.

c) Catalytic gas-phase oxidation of acrolein to acrylic acid

The catalytically active material calcined in b) was milled to a particle diameter of from 0.1 to 50 µm. Nonporous steatite spheres having a rough surface and a diameter of from 4 to 5 mm were coated in a rotary drum with the resulting powder of the active material in an amount of 50 g of powder per 200 g of steatite spheres, with simultaneous addition of 18 g of water.

Drying was then carried out with air maintained at 110° C. The coated catalyst thus obtained was diluted with a constant amount of inert material and used under the following reaction conditions in a tube-bundle reactor for the catalytic gas-phase oxidation of acrolein to acrylic acid:

Composition of the reaction gas:

5% by volume of acrolein, 7% by volume of $O_2$, 10% by volume of $H_2O$ and $N_2$ as the residual amount;

Space velocity: 2300 1(S.T.P.)per 1 per h.

The temperature of the salt bath used for heating was chosen so that an acrolein conversion of about 99 mol % resulted in the course of a single pass.

The table below shows the salt bath temperatures (BTemp) required for catalytically active materials obtained under various calcination conditions and the selectivity of the acrylic acid formation (S[%]) after an operating time of 4 weeks. The higher the required salt bath temperature, the lower is the catalyst activity. Furthermore, the table reflects the calcination conditions, in particular the average $NH_3$ content of the calcination atmosphere ($\overline{NH_3}$ [% by volume]).

TABLE

| Examples B, Comparative Ex. V | I (1) | O (g/l) | R (sec) | IF (l(S.T.P.)/h) | V (% by volume) | B Temp. (°C.) | S (%) | NH₃ (% by volume) |
|---|---|---|---|---|---|---|---|---|
| B1 | 3 | 250 | 86 | 125 | — | 260 | 94.8 | 4 |
| B2 | 3 | 50 | 86 | 125 | — | 272 | 93.9 | 1 |
| B3 | 3 | 250 | 43 | 250 | — | 265 | 94.2 | 2 |
| B4 | 3 | 250 | 135 | 80 | — | 257 | 95.3 | 6 |
| V1 | 40 | 19 | 78 | 1850 | — | 275 | 93.5 | 0.5 |
| B5 | 3 | 250 | 86 | 125 | 2 | 255 | 95.3 | 6 |
| V2 | 3 | 250 | 86 | 125 | 8 | 279 | 92.7 | 12 |

We claim:

1. A process for the preparation of a catalytically active poly-metal oxide material which contains the elements V and Mo in oxide form as basic components, in which an intimate dry mixture is prepared from starting compounds which contain the elemental constituents of the poly-metal oxide material and said mixture is calcined at from 300° to 450° C. in a gas atmosphere containing $O_2$ and $NH_3$, with the proviso that the gas atmosphere in which the calcination is carried out is composed of from 0.5 to 4% by volume of $O_2$ throughout the calcination, from 1 to 8% by volume, averaged over the total duration of the calcination, of $NH_3$, and steam or inert gas as the remaining amount.

2. A process as claimed in claim 1, wherein the calcination is carried out at a calcination temperature of from 300° to 350° C. for from 50 to 95% of the total calcination time (calcination stage I) and at a calcination temperature of from 380° to 450° C. for from 5 to 50% of the total calcination time in a subsequent calcination stage II, the $NH_3$ content of the calcination atmosphere averaged over the total duration of calcination stage I being from 5 to 8% by volume and the $NH_3$ content of the calcination atmosphere averaged over the total duration of calcination stage II being ≦4% by volume.

* * * * *